United States Patent
Okamoto et al.

(10) Patent No.: US 7,972,836 B2
(45) Date of Patent: Jul. 5, 2011

(54) METHOD OF ENZYMATIC OPTICAL RESOLUTION OF RACEMIC 4-HYDROXY-1,2,3,4-TETRAHYDROQUINOLINE

(75) Inventors: Masaki Okamoto, Osaka (JP); Akira Sakuragi, Osaka (JP); Muneki Kishida, Osaka (JP); Yoshikazu Mori, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 729 days.

(21) Appl. No.: 12/083,014

(22) PCT Filed: Oct. 4, 2006

(86) PCT No.: PCT/JP2006/319836
§ 371 (c)(1),
(2), (4) Date: Apr. 3, 2008

(87) PCT Pub. No.: WO2007/040238
PCT Pub. Date: Apr. 12, 2007

(65) Prior Publication Data
US 2009/0269821 A1    Oct. 29, 2009

(30) Foreign Application Priority Data

Oct. 4, 2005 (JP) .................... 2005-290757

(51) Int. Cl.
*C12P 41/00* (2006.01)
*C12P 17/18* (2006.01)
(52) U.S. Cl. ....................... 435/280; 435/119
(58) Field of Classification Search .............. None
See application file for complete search history.

(56) References Cited

FOREIGN PATENT DOCUMENTS

| EP | 0 748 805 A1 | 12/1996 |
|---|---|---|
| JP | 7-184685 | 7/1995 |
| JP | 8-322591 | 12/1996 |
| JP | 2001-149089 | 6/2001 |

OTHER PUBLICATIONS

European Search Report dated Sep. 23, 2010.

*Primary Examiner* — Sandra Saucier
(74) *Attorney, Agent, or Firm* — Finnegan, Henderson, Farabow, Garrett & Dunner, L.L.P.

(57) ABSTRACT

The present invention relates to a method for preparing an optically active 4-hydroxy-1,2,3,4-tetrahydroquinoline compound [I], which comprises the steps of:

treating a racemic 4-hydroxy-1,2,3,4-tetrahydroquinoline compound represented by general formula [I]:

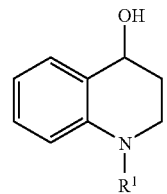

[wherein $R^1$ represents a hydrogen atom or a protecting group for amino group.]
with an enzyme having an ability of selectively or preferentially acylating one enantiomer of the racemic compound [I] in the presence of an acyl donor; and
if necessary, subjecting the reaction product to solvolysis.

9 Claims, No Drawings

METHOD OF ENZYMATIC OPTICAL RESOLUTION OF RACEMIC 4-HYDROXY-1,2,3,4-TETRAHYDROQUINOLINE

TECHNICAL FIELD

The present invention relates to a method for preparing an optically active 4-hydroxy-1,2,3,4-tetrahydroquinoline compound useful as a synthetic intermediate for pharmaceutical compounds such as optically active naphthalene compounds.

BACKGROUND ART

Generally, from the view point of intended pharmacological activities, side-effects and the like, pharmaceutical compounds having an asymmetric center in the molecule are desirable to be used in their optically active form instead of in racemic form. A racemic naphthalene compound (Patent literature 1) represented by general formula [A]:

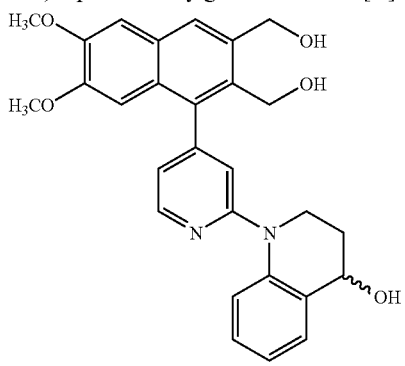

which is known to possess cAMP-specific phosphodiesterase (PDE4) inhibitory activity and be useful as anti-asthma drugs and the like, has one asymmetric carbon atom in the molecule, and therefore it is considered that the compound is desirable to be applied to clinical use in the optically active form.

It is known that the compound [A] can be obtained by reacting a compound represented by formula [B]:

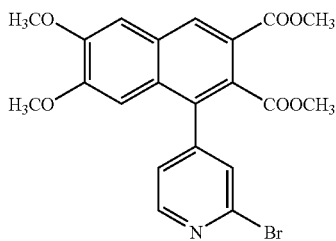

with 4(1H)-quinolinone compound represented by formula [C]:

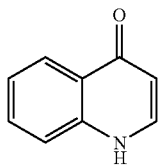

and then reducing the reaction product with sodium borohydride (Patent literature 1). However, the corresponding optically active form per se or a method for preparing the same (optical resolution methods of racemic form, asymmetric synthesis methods and the like) has not been reported so far.

From the viewpoint of synthetic chemistry, upon preparing an optically active form of the compound [A], there is considered a method of using an optically active form of 1,2,3,4-tetrahydroquinoline compound represented by general formula [I]:

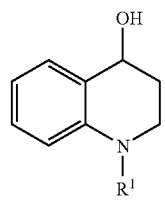

[wherein $R^1$ represents a hydrogen atom or a protecting group for amino group.]

as a synthetic intermediate, instead of using the compound [C]. However, the optically active compound [I] per se is a novel compound, and of course a method for preparing the same has not been reported so far. Under the circumstances, in order to establish a method for preparing an optically active form of the compound [A] comprising using the above-mentioned optically active compound [I], it is required to develop a method for preparing the optically active compound [I] with high optical purity and good yield.

[Patent literature 1] WO01/70700

DISCLOSURE OF THE INVENTION

Problems to be Solved by the Invention

An object of the present invention is to provide a method for preparing an optically active 4-hydroxy-1,2,3,4-tetrahydroquinoline compound useful as a synthetic intermediate for pharmaceutical compounds such as optically active naphthalene compounds, with industrial advantage. Also, the present invention provides a method for preparing an optically active naphthalene compound comprising using said optically active synthetic intermediate.

Means to Solve the Problems

The present invention relates to a method for preparing an optically active 4-hydroxy-1,2,3,4-tetrahydroquinoline compound [I], which comprises the steps of:

treating a racemic 4-hydroxy-1,2,3,4-tetrahydroquinoline compound represented by general formula [I]:

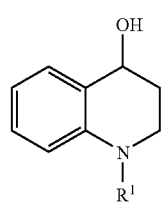

[wherein R¹ represents a hydrogen atom or a protecting group for amino group.]
with an enzyme having an ability of selectively or preferentially acylating one enantiomer of the racemic compound [I] in the presence of an acyl donor to obtain a mixture of a 4-hydroxy-1,2,3,4-tetrahydroquinoline compound represented by general formula [Ia]:

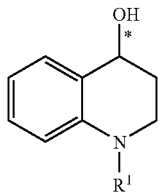

[Ia]

[wherein * represents an asymmetric carbon atom, and other symbols have the same meaning as defined above.] and a 4-acyloxy-1,2,3,4-tetrahydroquinoline compound represented by general formula [II]:

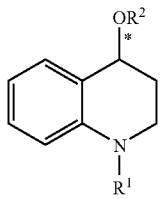

[II]

[wherein R² represents an acyl group, and other symbols have the same meaning as defined above.]
which is an acylated product of the corresponding enantiomer of the compound [Ia]; and
separating the compound [Ia] from the mixture, or separating the compound [II] from the mixture and then subjecting the compound [II] to solvolysis.

EFFECTS OF THE INVENTION

According to the present invention, an optically active 4-hydroxy-1,2,3,4-tetrahydroquinoline compound useful as a synthetic intermediate for pharmaceutical compounds such as optically active naphthalene compounds can be produced with high optical purity and good yield.

BEST MODE TO CARRY OUT THE INVENTION

In the present invention, R¹ of the racemic compound [I] is a hydrogen atom or a protecting group for amino group, and in particular, R¹ is preferably a protecting group for amino group. The protecting group for amino group may include a benzyloxycarbonyl group, a tert-butoxycarbonyl group, an acetyl group, a trifluoroacetyl group, a benzyl group, 9-fluorenylmethoxycarbonyl group and the like. Among them, preferred is a benzyloxycarbonyl group or a tert-butoxycarbonyl group, and particularly preferred is a benzyloxycarbonyl group.

As an enzyme having an ability of selectively or preferentially acylating one enantiomer of the racemic compound [I] (hereinafter also referred to as "an asymmetric acylating enzyme"), there may be any of an enzyme having an ability of selectively or preferentially acylating the (R)-enantiomer of the racemic compound [I], and an enzyme having an ability of selectively or preferentially acylating the (S)-enantiomer of the racemic compound [I].

The asymmetric acylating enzyme may include, for example, a group of enzymes referred to as a lipase or an esterase. The enzymes may be derived from microorganisms or derived from animal cells, and also may be derived from plant cells.

Also, the asymmetric acylating enzyme may be an extract extracted from microbial cells, animal cells or plant cells containing the enzyme according to known methods, and may be commercially available one.

The asymmetric acylating enzyme to be used in the method of the present invention is not particularly limited in its purity or state, and can be used in state such as purified enzymes, crude enzymes, a culture of microorganisms, microbial cells, or treated products of the microbial cells (lyophilized cells, acetone dried cells, autolyzed cells, cell-extracts, ground cells, and sonicated cells). Also, the microorganisms may be a wild strain or a mutant strain, and if necessary, may be those derived from the microorganisms by bioengineering techniques such as transgenesis and cell fusion. Further, the microbial cells or the treated products of the microbial cells can be used by being immobilized by known methods such as a polyacrylamide method, sulfur-containing polysaccharide gel method (carageenan gel method), alginic acid gel method and agar gel method.

Specific examples of the asymmetric acylating enzyme may include, for example, a lipase or an esterase derived from microorganisms belonging to the genus *Rhizopus*, the genus *Serratia*, the genus *Alcaligenes*, the genus *Candida*, the genus *Achromobacter*, the genus *Pseudomonas*, the genus *Humicola*, the genus *Burkholderia*, the genus *Mucor*, the genus *Aspergillus* or the genus *Penicillium*; a lipase or an esterase derived from porcine pancreas; and the like.

Among them, preferred is a lipase or an esterase derived from microorganisms belonging to the genus *Alcaligenes*, the genus *Candida*, the genus *Achromobacter*, the genus *Pseudomonas*, the genus *Humicola* or the genus *Burkholderia*.

The commercially available asymmetric acylating enzyme may include, for example, Esterase [derived from porcine pancreas, manufactured by Sigma-Aldrich Co.]; Talipase [derived from *Rhizopus delemar*, manufactured by Mitsubishi Tanabe Pharma Corporation]; Lipase SM [derived from *Serratia marcescens* Sr41, Japanese Examined Patent Publication No. 7-79690]; Lipase PL [derived from *Alcaligenes* sp., manufactured by Meito Sangyo Co., Ltd.]; Lipase QL [derived from *Alcaligenes* sp., manufactured by Meito Sangyo Co., Ltd.]; Lipase OF [derived from *Candida cylindraceae*, manufactured by Meito Sangyo Co., Ltd.]; Lipase AL [derived from *Achromobacter* sp., manufactured by Meito Sangyo Co., Ltd.]; Lipase P [derived from *Pseudomonas fluorescens*, manufactured by Amano Enzyme Inc.]; LPL [derived from *Pseudomonas* sp., manufactured by TOYOBO CO., LTD.]; CHIRAZYMEs L-2, L-5, L-8 or L-9 [derived from *Candida antarctica*, manufactured by Roche Diagnostics K.K.]; Lipase CE [derived from *Humicola languinosa*, manufactured by Amano Enzyme Inc.]; Lipase L [derived from *Candida lypolytica*, manufactured by Amano Enzyme Inc.]; Lipase PS [derived from *Burkholderia cepacia*, manufactured by Amano Enzyme Inc.]; Newlase [derived from *Rhizopus niveus*, manufactured by Amano Enzyme Inc.]; Lipase M [derived from *Mucor javanicus*, manufactured by Amano Enzyme Inc.]; Lipase AH [derived from *Burkholderia cepacia*, manufactured by Amano Enzyme Inc.]; Lipase AY [derived from *Candida cylindraceae*, manufactured by Amano Enzyme Inc.]; Lipase A [derived from *Aspergillus niger*, manufactured by Amano Enzyme Inc.]; Lipase R [derived from *Penicillium roqueforti*, manufactured by Amano Enzyme Inc.]; Lipase F-AP-15 [derived from *Rhizopus oryzae*, manufactured by Amano Enzyme Inc.]; Lipase G [derived from *Penicillium camembertii*, manufactured by Amano Enzyme Inc.]; Newlase F [derived from *Rhizopus niveus*, manufactured by Amano Enzyme Inc.]; Lipase Saiken 100 [derived from *Phizopus japonicus*, manufactured by NAGASE & CO., LTD.]; PPL (lipase derived from porcine pancreas) [derived from porcine pancreas, manufactured by Sigma-Aldrich Co.] and the like.

Among them, as an enzyme selectively or preferentially acylating the (R)-enantiomer of the racemic compound [I], preferred are Lipase PL, Lipase QL, Lipase AL, Lipase P, LPL, CHIRAZYME L-2, CHIRAZYME L-9, Lipase CE, Lipase PS, Lipase AH and the like. As an enzyme selectively or preferentially acylating the (S)-enantiomer of the racemic compound [I], CHIRAZYME L-5, etc. are preferred.

An amount of the asymmetric acylating enzyme to be used is not particularly limited, and usually is in the range of 0.1 to 20 parts by weight, preferably 0.5 to 5 parts by weight based on the racemic compound [I].

In the present invention, an acyl donor may include a carboxylic acid ester represented by general formula [III]:

[wherein $R^3$ and $R^4$ are the same or different and each represents an optionally substituted lower alkyl($C_1$-$C_6$) group, an optionally substituted lower alkenyl($C_2$-$C_6$) group or an optionally substituted lower alkynyl($C_2$-$C_6$) group.].

The lower alkyl group in $R^3$ and $R^4$ may include methyl group, ethyl group, n-propyl group, isopropyl group, n-butyl group and the like. The lower alkenyl group may include vinyl group, 1-propenyl group, allyl group, isopropenyl group and the like. The lower alkynyl group may include propargyl group and the like. The lower alkyl group, the lower alkenyl group, and the lower alkynyl group may be optionally substituted, and such a substituent may include a halogen atom(s) such as fluorine atom, chlorine atom, bromine atom and iodine atom.

Specific examples of the carboxylic acid ester may include, for example, vinyl acetate, propenyl acetate, trichloroethyl acetate, vinyl chloroacetate, propenyl chloroacetate, trichloroethyl chloroacetate and the like. Among them, vinyl acetate is particularly preferred.

An amount of the acyl donor to be used is in the range of 1 to 20 equivalent(s), preferably 1 to 5 equivalent(s) to the racemic compound [I].

Reactions are preferably conducted in the presence of a solvent. The solvent is not particularly limited so long as it can dissolve substrates without decreasing enzyme activities. The solvent may include, for example, cyclic or acyclic aliphatic ethers such as diethyl ether, diisopropyl ether, dibutyl ether, tert-butylmethylether, tetrahydrofuran, and dioxane; cyclic or acyclic aliphatic hydrocarbons such as hexane and cyclohexane; aromatic hydrocarbons such as benzene and toluene; nitriles such as acetonitrile and propionylnitrile; alkyl halides such as methylene chloride, chloroform, carbon tetrachloride and ethylene dichloride; esters such as ethyl acetate, butyl acetate and tert-butyl acetate; and ketones such as acetone and ethyl ethyl ketone. Among them, preferred are tert-butylmethylether, toluene, ethyl acetate or butyl acetate, and particularly preferred are ethyl acetate and butyl acetate.

An amount of the solvent to be used is in the range of 1 to 500 parts by weight, preferably 5 to 50 parts by weight based on the racemic compound [I].

Reactions are preferably conducted by mixing the racemic compound [I], the acyl donor, the asymmetric acylating enzyme and the solvent, and stirring the mixture at a given temperature. Reactions may be conducted in a batch system, or may be conducted in a continuous system using the immobilized asymmetric acylating enzyme. Reaction temperature is preferably in the range of 20 to 50° C., more preferably 25 to 40° C. Reaction time, which may differ depending on types of enzyme or solvent, or ratio of the substrate and the enzyme used, etc., is usually in the range of 5 to 90 hours, preferably 10 to 36 hours.

An optically active 4-hydroxy-1,2,3,4-tetrahydroquinoline compound [I] can be obtained by separating the compound [Ia] from the mixture of the compound [Ia] and the compound [II] which is an acylated product of the corresponding enantiomer of the compound [Ia]. Separation can be conducted in the same manner as usual methods used for separation/purification of organic compounds. For example, the objective optically active alcohol compound [I] can be obtained by adding water, hydrochloric acid and the like to the reaction solution to inactivate the enzyme, if necessary, and then extracting/concentrating the reaction product with a suitable solvent (ethyl acetate, toluene, etc.), and subjecting the resulting residue to purification by means of solvent extraction, column chromatography, fractional crystallization and the like.

Also, the optically active 4-hydroxy-1,2,3,4-tetrahydroquinoline compound [I] can be obtained by separating the compound [II] from the mixture of the compound [Ia] and the compound [II] obtained by the reaction, and then subjecting the compound [II] to solvolysis. In this case, the resulting optically active form is an enantiomer of the compound [Ia] in the mixture obtained by the enzyme reaction. Separation of the compound [II] from the mixture can be conducted in the same manner as above mentioned methods used for separation/purification of the optically active 4-hydroxy-1,2,3,4-tetrahydroquinoline compound [I].

Solvolysis can be conducted in the presence of a basic substance or an acidic substance. Such a basic substance may include, for example, amines such as triethylamine, hydrazine and pyridine, alkali metal alkoxides such as sodium methoxide and potassium tert-butoxide, alkali metal hydroxides such as sodium hydroxide and potassium hydroxide, and alkali metal carbonates such as sodium carbonate and potassium carbonate. Also, an acidic substance may include, for example, protonic acids such as hydrochloric acid and sulfuric acid, and Lewis acid such as titanium tetrachloride and boron trifluoride. An amount of the basic substance or the acidic substance to be used is not particularly limited, and is usually preferably in the range of 0.5 to 10 equivalent(s), more preferably 1.0 to 1.5 equivalent(s) to the compound [II].

Solvolysis is conducted in the presence of water, alcohol, or a mixture of water and alcohol. The alcohol may include methanol, ethanol, propanol, butanol and the like. An amount of water, alcohol or a mixture of water and alcohol to be used is not particularly limited, and is usually preferably in the range of 5 to 200 parts by weight based on the compound [II].

Solvolysis may be conducted in the presence of a solvent which has no influence on the reaction. Such a solvent may include, for example, alipthatic hydrocarbons such as hexane, heptane and cyclohexane, aromatic hydrocarbons such as benzene, toluene and xylene, and ethers such as diethyl ether, diisopropyl ether, tetrahydrofuran and 1,4-dioxane. The solvents may be used alone or in combination of two or more thereof. An amount of the solvent to be used is not particularly limited, and usually is preferably in the range of 1 to 200 times by weight based on the compound [II].

Reaction temperature is preferably in the range of 0 to 100° C., more preferably in the range of 20 to 50° C. Reaction time, which may differ depending on reaction conditions, is usually 10 minutes to 8 hours, preferably 20 minutes to 2 hours.

After the solvolysis, separation/purification of the optically active 4-hydroxy-1,2,3,4-tetrahydroquinoline compound [I] can be conducted according to conventional manners. For example, the objective optically active alcohol compound [I] can be obtained by subjecting the reaction solution to neutralization followed by concentration, if necessary, and then adding water thereto, extracting/concentrating the reaction product with a suitable solvent (ethyl acetate, toluene, etc.), and subjecting the resulting residue to purification by means of solvent extraction, column chromatography, fractional crystallization and the like.

An optically active 4-hydroxy-1,2,3,4-tetrahydroquinoline compound having a desired steric structure can be obtained by selecting the following properly:
selecting either an enzyme having an ability of selectively or preferentially acylating the (R)-enantiomer of the racemic compound [I] or an enzyme having an ability of selectively or preferentially acylating the (S)-enantiomer of the racemic compound [I] as an asymmetric acylating enzyme; and
separating the compound [Ia] from the resulting mixture, or separating the compound [II] and then subjecting it to solvolysis.

For example, (S)-4-hydroxy-1,2,3,4-tetrahydroquinoline compound can be obtained by using an enzyme having an ability of selectively or preferentially acylating the (R)-enantiomer of the racemic compound [I], and separating the compound [Ia] of the resulting mixture, while (R)-4-hydroxy-1,2,3,4-tetrahydroquinoline compound can be obtained by separating the compound [II] from the mixture and subjecting it to solvolysis.

On the other hand, (R)-4-hydroxy-1,2,3,4-tetrahydroquinoline compound can be obtained by using an enzyme having an ability of selectively or preferentially acylating the (S)-enantiomer of the racemic compound [I] and separating the compound [Ia] from the resulting mixture, while (S)-4-hydroxy-1,2,3,4-tetrahydroquinoline compound can be obtained by separating the compound [II] from the mixture and subjecting it to solvolysis.

Optionally, the obtained optically active 4-hydroxy-1,2,3,4-tetrahydroquinoline compound [I] may be modified by introducing a protecting group to a hydroxyl group at 4-position of the compound to form 1,2,3,4-tetrahydroquinoline compound represented by general formula:

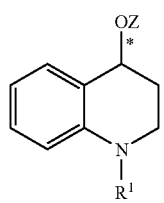

[IV]

[wherein Z represents a protecting group for hydroxyl group, and other symbols have the same meaning as defined above.].
The introduction of the protecting group can be conducted by conventional methods. For example, it may be conducted in the same manner as step (1) mentioned below.

The protecting group for hydroxyl group may include tert-butyldimethylsilyl group, trifluoroacetyl group, triethylsilyl group, tert-butoxycarbonyl group, benzyloxycarbonyl group, benzyl group and the like. Among them, tert-butyldimethylsilyl group is preferred.

Also, the introduction of a protecting group to a hydroxyl group at 4-position may be conducted after the enzyme reaction and before separation operation. For example, the optically active 4-hydroxy-1,2,3,4-tetrahydroquinoline compound [I] wherein the hydroxyl group is protected can be obtained in the following manner:

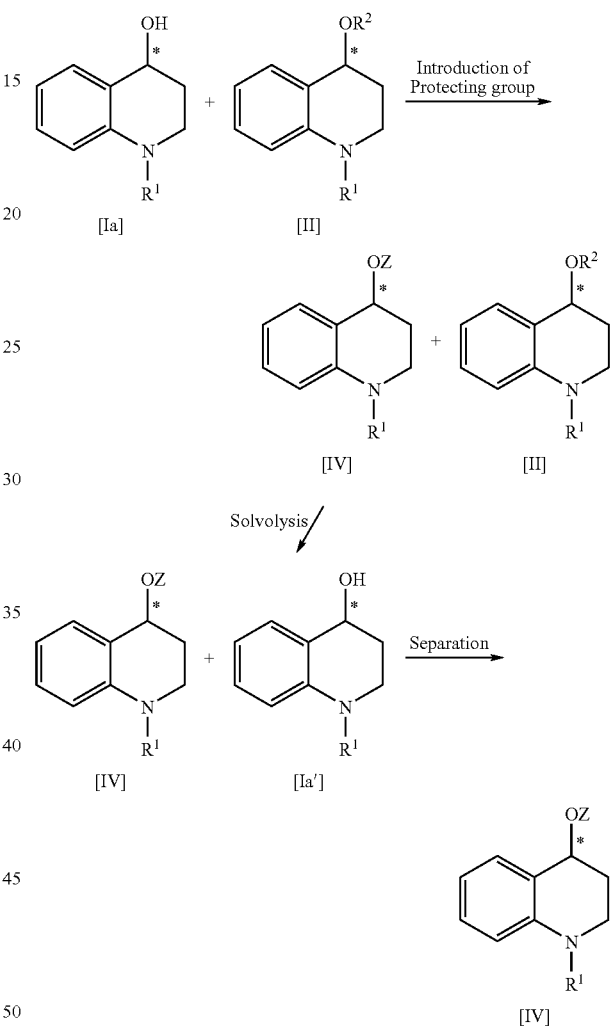

[wherein the symbols have the same meaning as defined above.]

After the enzyme reaction, a protecting group is introduced on the hydroxyl group of the compound [Ia] in the resulting mixture of the compound [Ia] and the compound [II] to make a mixture of the compound [IV] and the compound [II], and then the compound [II] in the mixture is subjected to solvolysis to obtain a mixture of the compound [IV] and the compound [Ia'] (the corresponding enantiomer of the compound [Ia] wherein the protecting group is introduced), and then the compound [IV] is separated from the mixture to obtain the optically active 4-hydroxy-1,2,3,4-tetrahydroquinoline compound [I] wherein the hydroxyl group is protected.

By using the optically active 4-hydroxy-1,2,3,4-tetrahydroquinoline compound [I] obtained as mentioned above, an optically active compound [A₁]:

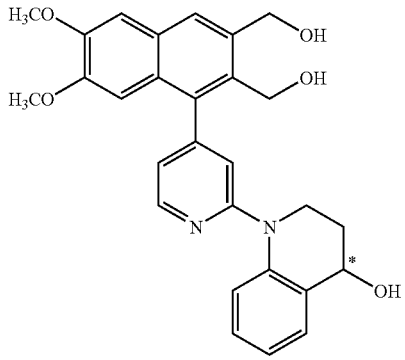

[wherein the symbols have the same meaning as defined above.]

of the naphthalene compound [A] can be prepared, for example, according to the following manners.

Namely, the optically active compound [A₁] can be prepared according to the following steps:

(1) introducing a protecting group to a hydroxyl group at 4-position of the obtained optically active 4-hydroxy-1,2,3,4-tetrahydroquinoline compound [I] to form a compound represented by general formula [IV]:

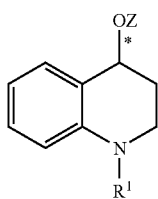

[wherein the symbols have the same meaning as defined above.];

(2) when the substituent (R¹) at 1-position of the compound [IV] is a protecting group for amino group, removing the protecting group to prepare an optically active tetrahydroquinoline compound represented by general formula [V]:

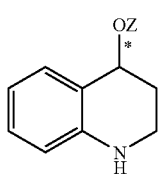

[wherein the symbols have the same meaning as defined above.];

(3) reacting the compound [V] with a compound represented by general formula [VI]:

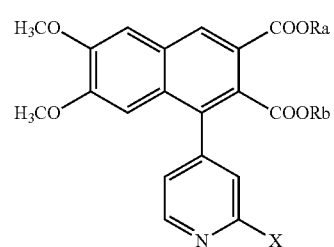

[wherein Ra and Rb are the same or different and each represents a hydrogen atom or a protecting group for carboxyl group, and X represents a halogen atom.]
to prepare an optically active naphthalene compound represented by general formula [VII]:

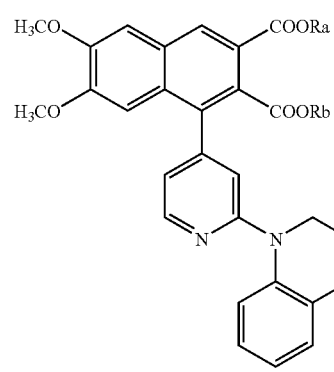

[wherein the symbols have the same meaning as defined above.];

(4) reducing the compound [VII] to prepare an optically active naphthalene compound represented by general formula [VIII]:

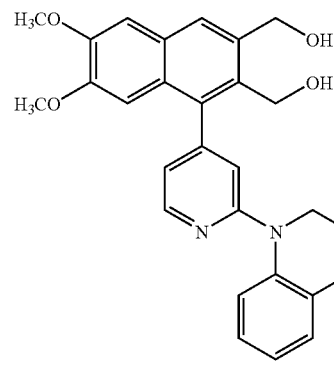

[wherein the symbols have the same meaning as defined above.]; and then (5) removing the protecting group Z for hydroxyl group from the compound [VIII].

The protecting group for carboxyl group may include, for example, a lower alkyl group and the like.

Step (1): The introduction of the protecting group (Z) to a hydroxyl group at 4-position of the optically active 4-hydroxy-1,2,3,4-tetrahydroquinoline compound [I] can be carried out according to the conventional manners. For example, the optically active 4-hydroxy-1,2,3,4-tetrahydroquinoline compound [I] and a halide corresponding to the protecting group (for example, tert-butyldimethylsilyl chloride) can be reacted in a suitable solvent (N,N-dimethylformamide, etc.) in the presence of a base (imidazole, etc.) at 0° C. to 50° C. for 30 minutes to 3 hours to prepare the compound [IV] wherein the protecting group (Z) is introduced on the hydroxyl group at 4-position.

Step (2): When 1-position of the compound [IV] is a protecting group for amino group, removal of the protecting group can be carried out according to conventional manners. For example, removal of the protecting group from the compound [IV] having a benzyloxycarbonyl group or a benzyl group as the protecting group can be carried out by subjecting the compound to catalytic hydrogenation reaction under the condition: in the presence of catalyst (palladium carbon, etc.), in a suitable solvent (ethanol, etc.), under a hydrogen atmosphere (1 atm to 3 atm), at 0° C. to 50° C., for 30 minutes to 3 hours.

Also, removal of the protecting group from the compound [IV] having a tert-butoxycarbonyl group as the protecting group can be carried out by reacting said compound with an acid (hydrochloric acid, etc.) in a suitable solvent (ether, etc.) at 0° C. to 50° C. for 30 minutes to 3 hours. Removal of the protecting group from the compound [IV] having an acetyl group, a trifluoroacetyl group or 9-fluorenylmethoxycarbonyl group as the protecting group can be carried out by hydrolyzing said compound with a base (sodium hydroxide, etc.) in a suitable solvent (hydrous ethanol, etc.) at 0° C. to 50° C. for 30 minutes to 3 hours.

Step (3): Reaction between the compound [V] and the compound [VI] can be carried out, for example, in a solvent in the presence of a palladium catalyst, a base and a phosphine ligand. Any solvent may be used so long as it has no influence on the present reaction. Such a solvent may include, for example, toluene, xylene, N,N-dimethylformamide, 1,4-dioxane, dimethylsulfoxide, 1-butanol, acetonitrile, or combination thereof, etc. The palladium catalyst may include, for example, palladium acetate, palladium chloride, bis(acetylacetonato)palladium, tris(dibenzylideneacetone)dipalladium, 1,1-bis(diphenylphosphino)ferrocene palladium dichloride and the like. The base may include, for example, alkali metal lower alkoxide such as sodium tert-butoxide, inorganic base such as cesium carbonate and potassium carbonate, and the like. The phosphine ligand may include, for example, tri-(tert-butyl)phosphonium-tetrafluoroborate, di-(tert-butyl)phosphonium-tetrafluoroborate, tri-(n-butyl) phosphonium-tetrafluoroborate, tri-(tert-butyl)phosphine and the like.

An amount of the compound [V] to be used is 1.0 to 2.0 equivalent(s), preferably 1.1 to 1.5 equivalents to the compound [VI]. An amount of the palladium catalyst to be used is 0.01 to 1 equivalent, preferably 0.02 to 0.2 equivalent to the compound [V] or the compound [VI]. An amount of the base to be used is 0.5 to 5 equivalent(s), preferably 1 to 2 equivalent(s) to the compound [V] or the compound [VI]. An amount of the phosphine ligand to be used is 0.01 to 0.5 equivalent, preferably 0.02 to 0.1 equivalent to the compound [V] or the compound [VI].

Reaction temperature of the present reaction is 25 to 150° C., preferably 80 to 120° C. Reaction time, which may differ depending on reaction conditions, is usually 10 minutes to 8 hours, preferably 30 minutes to 6 hours.

Step (4): Reduction of the compound [VII] can be carried out in a solvent in the presence of a reducing agent. Any solvent can be used so long as it has no influence on the present reaction. Such a solvent may include, for example, methanol, tetrahydrofuran, ethanol, N,N-dimethylformamide, dimethylsulfoxide, 1,2-dimethoxy ethane, or combination thereof, etc. The reducing agent may include, for example, metal hydride such as sodium borohydride, sodium bis(2-methoxyethoxy)aluminum hydrate, and lithium aluminium hydride, etc. An amount of the reducing agent to be used is 1 to 30 equivalent(s), preferably 5 to 20 equivalents to the compound [VII].

Reaction temperature of the present reaction is 0 to 60° C., preferably 15 to 40° C. Reaction time, which may differ depending on reaction conditions, is usually 10 minutes to 8 hours, preferably 30 minutes to 5 hours.

Step (5): Removal of the protecting group Z from the compound [VIII] can be carried out, like the removal reaction of the protecting group for amino group in the above step (2), depending on the variety of the protecting group, by conventional manners such as hydrolysis (when the protecting group is an acetyl group), acid treatment (when the protecting group is triethylsilyl group or tert-butoxycarbonyl group) and reduction (when the protecting group is a benzyloxycarbonyl group or a benzyl group). Also, when the protecting group is tert-butyldimethylsilyl group, the protecting group can be easily removed, for example, by the reaction in acetic acid in the presence of tetrabutylammonium fluoride.

The racemic compound [I] which is the starting material of the present invention can be prepared by reducing 2,3-dihydro-4-quinolone compound represented by general formula [IX]:

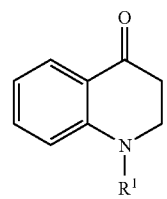

[IX]

[wherein the symbols have the same meaning as defined above.].

The reduction can be conducted by the reaction in the presence of a reducing agent such as sodium borohydride, lithium borohydride, lithium aluminum hydride and diisobutylaluminum hydride. The present reaction can proceed suitably, for example, at 0 to 60° C., particularly at 15 to 40° C. Reaction time, which may differ depending on reaction conditions, is usually 10 minutes to 8 hours, preferably 30 minutes to 5 hours.

The objective compounds of the respective reactions mentioned above can be subjected to separation/purification according to conventional manners. For example, the objective compounds of the respective reactions can be obtained by subjecting the reaction solution to neutralization followed by concentration, if necessary, and then adding water thereto and extracting/concentrating the reaction product with a suitable solvent (ethyl acetate, toluene, etc.), and subjecting the resulting residue to solvent extraction, column chromatography, crystallization in a suitable solvent and the like.

Incidentally, the raw material compound [IX] in the present invention can be prepared, for example, according to the method described in Journal of Medicinal Chemistry, Vol. 8, pp. 566-571 (1965). Also, the raw material compound [VI]

can be prepared, for example, according to the method described in European Patent No. 748805.

EXAMPLES

In the following, the present invention is explained in more detail by the following examples, but the examples do not limit the present invention.

Example 1

About 10 mg of enzyme shown in the following Table 1 was weighed into a test tube. At the same time, 4 mg of racemic 1-benzyloxycarbonyl-4-hydroxy-1,2,3,4-tetrahydroquinoline and 6 mg of vinyl acetate were dissolved in 1 mL of tert-butylmethylether. The solution was added to the test tube wherein the enzyme has been weighed in advance, and the test tube was shaken at 30° C. for about 20 hours. The reaction solution was centrifuged, and the supernatant was sampled and subjected to HPLC analysis.

HPLC measurement condition
Column: CHIRALPAK AD-H (4.6×250 mm)
Mobile phase: n-hexane/ethanol=10:1
Column temperature: 40° C.
Flow rate: 11.0 mL/min
Detection wavelength: 254 nm Retention times of the (S)-4-hydroxy compound, the (R)-4-hydroxy compound and the 4-acetoxy compound were 19.6 minute, 26.8 minute, and 9.4 minute, respectively.

The results are shown in Table 1. Conversion ratio (%) means a ratio that the 4-hydroxy compound has been converted to the 4-acetoxy compound, and was calculated by the following equation.

Conversion ratio (%)=[4-acetoxy compound (% by area)]/[4-hydroxy compound (% by area)+4-acetoxy compound (% by area)]×100

Optical purity (% ee) means enantiomeric excess of the (S)-4-hydroxy compound, and was calculated from the following equation.

Optical purity (% ee)=[(S)-4-hydroxy compound (% by area)-(R)-4-hydroxy compound (% by area)]/[(S)-4-hydroxy compound (% by area)+(R)-4-hydroxy compound (% by area)]×100

TABLE 1

| Enzyme name | Conversion ratio (%) | Optical purity (% ee) |
|---|---|---|
| Lipase PL [derived from *Alcaligenes* sp., manufactured by Meito Sangyo Co., Ltd.] | 71.8 | 94.6 |
| Lipase AL [derived from *Achromobacter* sp., manufactured by Meito Sangyo Co., Ltd.] | 54.9 | 96.0 |
| Lipase P [derived from *Pseudomonas fluorescens*, manufactured by Amano Enzyme Inc.] | 44.5 | 84.7 |
| LPL [derived from *Pseudomonas* sp., manufactured by TOYOBO CO., LTD.] | 87.0 | 88.4 |
| CHIRAZYME L-9 [derived from *Candida antarctica*, manufactured by Roche Diagnostics K.K.] | 59.3 | 100.0 |
| Lipase CE [derived from *Humicola languinosa*, manufactured by Amano Enzyme Inc.] | 42.3 | 78.1 |

TABLE 1-continued

| Enzyme name | Conversion ratio (%) | Optical purity (% ee) |
|---|---|---|
| Lipase PS [derived from *Burkholderia cepacia*, manufactured by Amano Enzyme Inc.] | 55.9 | 96.7 |
| Lipase AH [derived from *Burkholderia cepacia*, manufactured by Amano Enzyme Inc.] | 45.9 | 80.5 |

Example 2

A racemic 4-hydroxy-1-tert-butoxycarbonyl-1,2,3,4-tetrahydroquinoline was used as a substrate, and was reacted with the enzymes shown in the following Table 2 in the same manner as Example 1. Results are shown in the following Table 2.

TABLE 2

| Enzyme name | Conversion ratio (%) | Optical purity (% ee) |
|---|---|---|
| Lipase PL [derived from *Alcaligenes* sp., manufactured by Meito Sangyo Co., Ltd.] | 55.5 | 85.4 |
| LPL [derived from *Pseudomonas* sp., manufactured by TOYOBO CO., LTD.] | 74.1 | 100.0 |
| CHIRAZYME L-2 [derived from *Candida antarctica*, manufactured by Roche Diagnostics K.K.] | 41.5 | 76.0 |
| CHIRAZYME L-9 [derived from *Candida antarctica*, manufactured by Roche Diagnostics K.K.] | 57.8 | 100.0 |
| Lipase PS [derived from *Burtholderia cepacia*, manufactured by Amano Enzyme Inc.] | 46.3 | 76.8 |
| Lipase AH [derived from *Burkholderia cepacia*, manufactured by Amano Enzyme Inc.] | 49.6 | 100.0 |

Example 3

Reaction was conducted in the same manner as Example 1 using the enzyme shown in the following Table 3. Results are shown in the following Table 3. Incidentally, optical purity (% ee) means enantiomeric excess of the (R)-4-hydroxy compound.

TABLE 3

| Enzyme name | Conversion ratio (%) | Optical purity (% ee) |
|---|---|---|
| CHIRAZYME L-5 [derived from *Candida antarctica*, manufactured by Roche Diagnostics K.K.] | 73.2 | 94.5 |

Example 4

Asymmetric acylation reaction (reaction time: 90 hours) was conducted in the same manner as Example 1 using the enzymes shown in the following Table 4, and using butyl acetate or toluene as a reaction solvent. Incidentally, the measurements of the conversion ratio and the optical purity were conducted 24 hours and 90 hours after the reaction initiation.

Results are shown in the following Table 4. Incidentally, optical purity means enantiomeric excess of the (S)-4-hydroxy compound.

TABLE 4

| Enzyme name | Solvent | Conversion ratio (%) | | Optical purity (% ee) | |
|---|---|---|---|---|---|
| | | 24 hours | 90 hours | 24 hours | 90 hours |
| Lipase PL [derived from *Alcaligenes* sp., manufactured by Meito Sangyo Co., Ltd.] | Butyl acetate | 44.8 | 53.8 | 69.4 | 87.6 |
| Lipase QL [derived from *Alcaligenes* sp., manufactured by Meito Sangyo Co., Ltd.] | Butyl acetate | 39.2 | 70.2 | 38.3 | 67.2 |
| Lipase AL [derived from *Achromobacter* sp., manufactured by Meito Sangyo Co., Ltd.] | Butyl acetate | 29.5 | 44.7 | 41.8 | 77.3 |
| LPL [derived from *Pseudomonas* sp., manufactured by TOYOBO CO., LTD.] | Butyl acetate | 52.7 | 60.1 | 94.7 | 93.2 |
| | Toluene | 42.4 | 49.5 | 75.8 | 93.9 |
| CHIRAZYME L-2 [derived from *Candida antarctica*, manufactured by Roche Diagnostics K.K.] | Butyl acetate | 29.7 | 45.6 | 43.4 | 86.9 |
| | Toluene | 29.3 | 40.0 | 42.1 | 69.5 |
| CHIRAZYME L-9 [derived from *Candida antarctica*, manufactured by Roche Diagnostics K.K.] | Butyl acetate | 24.7 | 42.4 | 30.6 | 68.5 |
| | Toluene | 31.7 | 48.8 | 44.0 | 86.1 |
| Lipase PS [derived from *Burkholderia cepacia*, manufactured by Amano Enzyme Inc.] | Butyl acetate | 26.3 | 48.0 | 35.7 | 90.4 |
| | Toluene | 39.3 | 52.9 | 66.9 | 94.5 |

Example 5

Asymmetric acylation reaction (reaction time: 90 hours) was conducted in the same manner as Example 1 using the enzyme shown in the following Table 5, and using toluene as a reaction solvent. Incidentally, the measurements of the conversion ratio and the optical purity were conducted 24 hours and 90 hours after the reaction initiation. Results are shown in the following Table 5. Incidentally, optical purity means enantiomeric excess of the (R)-4-hydroxy compound.

TABLE 5

| Enzyme name | Conversion ratio (%) | | Optical purity (% ee) | |
|---|---|---|---|---|
| | 24 hours | 90 hours | 24 hours | 90 hours |
| CHIRAZYME L-5 [derived from *Candida antarctica*, manufactured by Roche Diagnostics K.K.] | 20.5 | 64.5 | 23.8 | 97.3 |

Example 6

(1) To a flask were charged 2.00 g of racemic 1-benzyloxycarbonyl-4-hydroxy-1,2,3,4-tetrahydroquinoline and 40 mL of ethyl acetate, and the mixture was stirred. After confirming dissolution, 11.0 g of CHIRAZYME L-2 was added thereto and incubated in a water bath at 30° C. After the temperature became constant, 1.82 g of vinyl acetate was added thereto and stirred for 18 hours. To the reaction solution was added 10 mL of saturated aqueous sodium bicarbonate solution, and the solution was subjected to extraction/separation, and the organic layer was washed with water, and to it was added MgSO₄ and the insoluble material was filtered. The filtrate was concentrated under reduced pressure to give 2.10 g of a mixture of (S)-1-benzyloxycarbonyl-4-hydroxy-1,2,3,4-tetrahydroquinoline and (R)-4-acetoxy-1-benzyloxycarbonyl-1,2,3,4-tetrahydroquinoline as yellow oil (estimated yield 93%, 99.8% ee).

(2) To a flask were charged 2.10 g of the mixture obtained in the above (1), 6 mL of N,N-dimethylformamide and 0.449 g of imidazole, and the mixture was dissolved in a water bath at 40° C. To it was added dropwise a mixed solution of 0.846 g of tert-butyldimethylsilyl chloride and 3 mL of N,N-dimethylformamide. After about 6 hours, termination of the reaction was confirmed by TLC. To the reaction solution were added 10 mL of 10% aqueous citric acid solution and 40 mL of ethyl acetate, and the mixture was subjected to extraction/separation, and to the organic layer was added 10 mL of saturated aqueous sodium bicarbonate solution, which was subjected to extraction/separation. To the organic layer was dried over MgSO₄, and the insoluble material was filtered. The filtrate was concentrated under reduced pressure to give 2.53 g of mixture of (S)-1-benzyloxycarbonyl-4-tert-butyldimethylsilyloxy-1,2,3,4-tetrahydroquinoline and (R)-4-acetoxy-1-benzyloxycarbonyl-1,2,3,4-tetrahydroquinoline as yellow oil (100% yield).

(3) To 2.53 g of the mixture obtained in the above (2) was added 25 mL of methanol, and the mixture was incubated under stirring in a water bath wherein the temperature was maintained constant at 50° C. To it was added dropwise a solution of 0.547 g of potassium carbonate in 12.5 mL of water. After about 20 minutes, termination of the reaction was confirmed by TLC, and to the reaction solution was added 80 mL of ethyl acetate, and it was subjected to extraction/separation, and the organic layer was washed with 10 mL of water twice. To the organic layer was dried over MgSO₄, and the insoluble material was filtered. The filtrate was concentrated under reduced pressure to give 2.25 g of mixture of (S)-1-benzyloxycarbonyl-4-tert-butyldimethylsilyloxy-1,2,3,4-tetrahydroquinoline and (R)-4-hydroxy-1-benzyloxycarbonyl-1,2,3,4-tetrahydroquinoline as yellow oil.

(4) To 2.25 g of the mixture obtained in the above (3) was added 12 mL of dimethylsulfoxide and the mixture was mixed, and to the mixture was added 40 mL of n-hexane, which was subjected to extraction, and then the n-hexane layer was separated by decantation. Further, the extraction operation was conducted with 40 mL of n-hexane twice followed by 20 mL of n-hexane twice. The n-hexane layers were combined, and to it was added 2 mL of dimethylsulfoxide, which was subjected to extraction/separation, and the hexane layer was washed with 2 mL of water twice. To the hexane layer was dried over $MgSO_4$, and the insoluble material was filtered. The filtrate was concentrated under reduced pressure to give 1.30 g of (S)-1-benzyloxycarbonyl-4-tert-butyldimethylsilyloxy-1,2,3,4-tetrahydroquinoline as colorless oil (49% yield, including about 5% by weight of dimethylsulfoxide). The optical purity measurement of the compound was conducted by HPLC, and the optical purity was >99% ee.

HPLC measurement condition
Column: CHIRALCEL OJ-H (4.6×150 mm)
Mobile phase: n-hexane/ethanol=100:1
Column temperature: 40° C.
Flow rate: 1.0 mL/min
Detection wavelength: 254 nm Example 7

(1) To a solution of 39.28 g of (S)-1-benzyloxycarbonyl-4-tert-butyldimethylsilyloxy-1,2,3,4-tetrahydroquinoline in 393 mL of ethanol was added 1.96 g of palladium carbon under a nitrogen atmosphere, and then the mixture was stirred under a hydrogen atmosphere for 4 hours. The reaction solution was filtered, and the filtrate was concentrated. The resulting residue was purified by column chromatography on silica gel (solvent; n-hexane/ethyl acetate=30/1 to 20/1) to give 14.82 g of (S)-4-tert-butyldimethylsilyloxy-1,2,3,4-tetrahydroquinoline (yield: 56.9%, optical purity: 98.8% ee).
$[\alpha]_D^{28}=-128.6°$ (methanol, c=1.10)
$^1$H-NMR ($CDCl_3$) δ: 7.13 (d, J=7.7 Hz, 1H), 7.04 (t, J=6.9 Hz, 1H), 6.63 (t, J=7.4 Hz, 1H), 6.48 (d, J=7.7 Hz, 1H), 4.78 (t, J=4, 4 Hz, 1H), 3.7-3.9 (br, 1H), 3.41-3.45 (m, 1H), 3.24-3.28 (m, 1H), 1.18-1.94 (m, 2H), 0.91 (s, 9H), 0.15 (s, 3H), 0.10 (s, 3H)

Also, the optical purity (enantiomeric excess: ee) of the objective substance was measured under the following condition.
Column used: CHIRALCEL OJ-H (DAICEL CHEMICAL INDUSTRIES, LTD.)
Mobile phase: methanol/n-hexane=1/99
(2) A solution of 20.00 g of 1-(2-bromo-4-pyridyl)-2,3-bis(methoxycarbonyl)-6,7-dimethoxynaphthalene in 200 mL of toluene was sonicated under reduced pressure, and then to the solution were added 975 mg of palladium acetate, 1009 mg of tri-tert-butylphosphonium tetrafluoroborate, 13.72 g of the compound obtained in the above (1) and 6.26 g of sodium tert-butoxide at room temperature. After nitrogen substitution, the mixture was stirred at 100° C. for 4 hours. After radiation, to the reaction solution were added 100 mL of saturated aqueous ammonium chloride solution, 100 mL of water and 100 mL of ethyl acetate, and the mixture was filtered through Celite®. Celite® was washed with 100 mL of ethyl acetate, and then the organic layer was separated. The organic layer was washed with 100 g of 20% saline, dried over magnesium sulfate, and then concentrated. The resulting residue was purified by column chromatography on silica gel (n-hexan/ethyl acetate=5/1 to 4/1) to give 22.31 g of 1-[2-[(4S)-4-(tert-butyldimethylsilyloxy)-1,2,3,4-tetrahydroquinolin-1-yl]-4-pyridyl]-2,3-bis(methoxycarbonyl)-6,7-dimethoxynaphthalene (yield: 80%).
MS (APCI) m/z: 643[M+H]$^+$
$[\alpha]_D^{28}=-62°$ (methanol, c=1)
(3) To a solution of 21.21 g of the compound obtained in the above (2) in 212 mL of tetrahydrofuran was added 8.74 g of sodium borohydride at room temperature, and then to the solution was added dropwise 16.9 mL of methanol at 60° C. over 2 hours. Furthermore, to the reaction solution was added 8.74 g of sodium borohydride at the same temperature, and to it was added dropwise 16.9 mL of methanol over 2 hours. After radiation, to the reaction solution was added 212 g of 20% saline, which was extracted with 212 mL of ethyl acetate. The aqueous layer was extracted with 212 mL of ethyl acetate, and the combined organic layers were washed with 212 g of 20% saline, dried over 10.6 g of magnesium sulfate, and then concentrated under reduced pressure. The resulting residue was purified by column chromatography on silica gel (solvent; n-hexan/ethyl acetate=1/1 to 2/1) to give 17.86 g of 1-[2-[(4S)-4-(tert-butyldimethylsilyloxy)-1,2,3,4-tetrahydroquinolin-1-yl]-4-pyridyl]-2,3-bis(hydroxymethyl)-6,7-dimethoxynaphthalene (yield: 92%).
MS (APCI) m/z: 587[M+H]$^+$
$[\alpha]_D^{28}=-77°$ (methanol, c=1)
(4) To 17.00 g of the compound obtained in the above (3) were added 8.3 mL of acetic acid and 289 mL of 1M tetrabutylammonium fluoride-tetrahydrofuran solution in water bath, and the mixture was stirred at room temperature for 4 hours. To the reaction solution was added further 145 mL of 1M tetrabutylammonium fluoride-tetrahydrofuran solution at room temperature, and the mixture was stirred at the same temperature for 2 hours. To the reaction solution were added 6% aqueous sodium hydrogen carbonate solution and 25% saline, which was extracted with ethyl acetate. The extracts were dried over magnesium sulfate and then filtered, and the filtrate was concentrated under reduced pressure. The resulting residue was purified by column chromatography on silica gel (solvent; chloroform/methanol=99/1 to 96/4) to give 10.4 g of 1-[2-[(4S)-4-hydroxy-1,2,3,4-tetrahydroquinolin-1-yl]-4-pyridyl]-2,3-bis(hydroxymethyl)-6,7-dimethoxynaphthalene (yield: 72%) as a crude product. To a solution of 10.2 g of the compound in 30.6 mL of ethanol was added 10.6 mL of water at 40° C. After precipitating crystals, 306 mL of water was further added and the mixture was cooled. The precipitated crystals were collected by filtration and washed with 20.6 mL of water, and then dried under reduced pressure at room temperature to give 8.66 g of 1-[2-[(4S)-4-hydroxy-1,2,3,4-tetrahydroquinolin-1-yl]-4-pyridyl]-2,3-bis(hydroxymethyl)-6,7-dimethoxynaphthalene sesquihydrate (yield: 85%, optical purity: 99.9% ee) as crystals.
MS (APCI) m/z: 493[M+H]$^+$
$[\alpha]_D^{22}=-92.2°$ (methanol, c=1)
Water content: 5.35% (Karl Fischer's method)
$^1$H-NMR ($CDCl_3$) δ: 8.46 (t, J=5.3 Hz, 1H), 7.71 (d, J=6.6 Hz, 1H), 7.37-7.39 (m, 2H), 7.18 (s, 1H), 7.13 (d, J=8.2 Hz, 1H), 7.05-7.10 (m, 1H), 6.85-6.95 (m, 1H), 6.80-6.85 (m, 1H), 6.71 (d, J=14.8 Hz, 1H), 4.79-4.93 (m, 3H), 4.58-4.70 (m, 2H), 4.22-4.25 (m, 1H), 4.00 (d, J=6.9 Hz, 3H), 3.88-3.99 (m, 1H), 3.78 (d, J=17.9 Hz, 3H), 3.03-3.11 (br, 2H), 2.03-2.16 (m, 3H)

Also, the optical purity (enantiomeric excess: ee) of the objective substance was measured under the following condition.

Column used: SUMICHIRAL OA-4900 (Sumika Chemical Analysis Service, Ltd.)
Mobile Phase:
n-hexan/ethanol/tetrahydrofuran/trifluoroacetic acid=350/100/50/1

Reference Example 1

To a flask were charged 25.04 g of 1-benzyloxycarbonyl-2,3-dihydro-4-quinolone, 6.72 g of sodium borohydride and 200 mL of tetrahydrofuran, and the flask was incubated in a water bath wherein the temperature was maintained constant at 25° C. To the flasks was added dropwise 50 mL of methanol over about 30 minutes with watching out heat generation/foam formation. After confirming the reaction termination by TLC, to the flask was added dropwise 400 mL of water with watching out foam formation, and to the solution was added 800 mL of ethyl acetate and the objective product was extracted. Further, the organic layer was washed with 2.5% saline, and then to the organic layer was added $MgSO_4$, and the insoluble material was filtered. The filtrate was concentrated under reduced pressure to give 24.05 g of 1-benzyloxycarbonyl-4-hydroxy-1,2,3,4-tetrahydroquinoline as white solid (86% yield).

Reference Example 2

(1) To a solution of 500 g of 3,4-dimethoxybenzaldehyde in 2.5 L of methanol was added dropwise 529 g of bromine at room temperature (under cooled condition, if necessary) over 1 hour, and the mixture was stirred at the same temperature for 3 hours. To the reaction solution was added dropwise 2.5 L of water, and the crystals were precipitated. To a suspension of the crystal was added 20% aqueous sodium hydroxide solution at room temperature to adjust it to pH about 9 to 10, and then cooled. The precipitated crystals were collected by filtration and washed with water, and then dried at 50° C. for 12 hours to give 718.78 g of 6-bromo-3,4-dimethoxybenzaldehyde (yield: 98%).

(2) To a suspension of 612.68 g of the compound obtained in the above (1), 397.88 g of trimethyl orthoformate and 612 mL of methanol was added 4.76 g of p-toluenesulfonic acid, and the mixture was refluxed under heating for 3 hours. After radiation, to the mixture was added 2.70 g of 28% sodium methylate-methanol solution, and the mixture was concentrated. The residue was dissolved in 1.2 L of toluene, and the solution was concentrated. The residue was dissolved in 1.2 L of toluene again and the solution was concentrated to give 762.85 g of 6-bromo-3,4-dimethoxybenzaldehyde dimethylacetal (yield: quantitative).

(3) To a solution of 2.91 g of the compound obtained in the above (2) in 9 mL of tetrahydrofuran was added dropwise 6.25 mL of 1.6M n-butyl lithium-hexan solution under a nitrogen atmosphere under dry ice-acetone cooled condition, and the mixture was stirred at the same temperature for 30 minutes. To the reaction solution was added dropwise a solution of 1.86 g of 2-bromo-4-formylpyridine in 9 mL of tetrahydrofuran, and the mixture was stirred for 1 hour. To the reaction solution was added 30 mL of saturated aqueous ammonium chloride solution, and the solution was extracted with 30 mL of ethyl acetate. The aqueous layer was extracted with 30 mL of ethyl acetate again, and the extracts were combined and washed with saturated saline, then dried over magnesium sulfate, and concentrated under reduced pressure. The residue was triturated with 100 mL of chloroform and concentrated under reduced pressure. The residue was purified by column chromatography on silica gel (solvent; n-hexan/ethyl acetate=3/1 to 1/1) to give 2.53 g of 3,4-dimethoxy-6-(2-bromo-4-pyridyl)(hydroxy)methylbenzaldehyde dimethylacetal (yield: 64%).

(4) A mixture of 4.00 g of the compound obtained in the above (3), 1.59 g of dimethyl fumarate, 20 mL of xylene and 2 g of acetic acid was refluxed under heating for 2 hours. After radiation, the reaction solution was concentrated under reduced pressure. To the residue was added 8 mL of toluene, and the solution was concentrated. To the resulting residue was added 8 mL of acetonitrile, and then added dropwise 3.55 g of boron trifluoride-diethylether in an ice-water bath. The mixture was refluxed under heating for 2 hours. After radiation the reaction solution was concentrated under reduced pressure. To the residue was added 28 mL of chloroform, which was ice-cooled. To the mixture was added dropwise 3.41 g of 25% aqueous ammonia at 25° C. or below, and then the mixture was stirred at 45 to 50° C. for 15 minutes. To the reaction solution was added 24 mL of water, and then the organic layer was washed with 20 mL of water and 28 g of 20% saline, dried over magnesium sulfate, and then concentrated under reduced pressure. To the resulting residue was added 12 mL of methanol and the mixture was heated. The solution was cooled, and the precipitated crystals were collected by filtration to give 3.67 g of 1-(2-bromo-4-pyridyl)-2,3-bis(methoxycarbonyl)-6,7-dimethoxynaphthalene (yield: 79.7%) as crystals.

UTILIZABILITY IN INDUSTRY

According to the present invention, an optically active 4-hydroxy-1,2,3,4-tetrahydroquinoline compound useful as a synthetic intermediate for pharmaceutical compounds such as an optically active naphthalene compound (PDE4 inhibitor) can be prepared with industrial advantage.

The invention claimed is:
1. A method for preparing an optically active 4-hydroxy-1,2,3,4-tetrahydroquinoline compound [I], which comprises the steps of:
treating a racemic 4-hydroxy-1,2,3,4-tetrahydroquinoline compound represented by formula [I]:

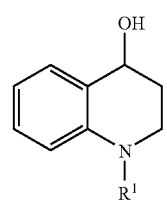

wherein $R^1$ represents a hydrogen atom or a protecting group for the amino group,
with an enzyme having an ability of selectively or preferentially acylating one enantiomer of the racemic compound [I] in the presence of an acyl donor to obtain a mixture of a 4-hydroxy-1,2,3,4-tetrahydroquinoline compound represented by formula [Ia]:

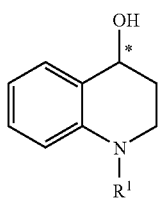

[Ia]

wherein * represents an asymmetric carbon atom,
and a 4-acyloxy-1,2,3,4-tetrahydroquinoline compound represented by formula [II]:

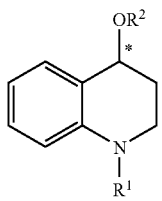

[II]

wherein $R^2$ represents an acyl group,
which is an acylated product of the corresponding enantiomer of the compound [Ia]; and
separating the compound [Ia] from the mixture, or
separating the compound [II] from the mixture and then subjecting the compound [II] to solvolysis.

2. The method according to claim 1, wherein the enzyme is an enzyme having an ability of selectively or preferentially acylating the (R)-enantiomer of the racemic compound [I] in the presence of an acyl donor.

3. The method according to claim 1, wherein the enzyme is an enzyme having an ability of selectively or preferentially acylating the (S)-enantiomer of the racemic compound [I] in the presence of an acyl donor.

4. The method according to claim 1, comprising separating the compound [Ia] from the mixture.

5. The method according to claim 1, comprising separating the compound [II] from the mixture and then subjecting the compound [II] to solvolysis.

6. The method according to claim 1, wherein the acyl donor is a carboxylic acid ester represented by general formula [III]:

$R^3COOR^4$ [III]

wherein $R^3$ and $R^4$ are the same or different and each represents an optionally substituted lower alkyl group, an optionally substituted lower alkenyl group or an optionally substituted lower alkynyl group.

7. The method according to claim 6, wherein $R^3$ is methyl group, and $R^4$ is vinyl group in the general formula [III].

8. The method according to claim 1, wherein the enzyme having an ability of selectively or preferentially acylating one enantiomer of the racemic compound [I] is a lipase or an esterase derived from microorganisms belonging to the genus *Rhizopus*, the genus *Serratia*, the genus *Alcaligenes*, the genus *Candida*, the genus *Achromobacter*, the genus *Pseudomonas*, the genus *Humicola*, the genus *Burkholderia*, the genus *Mucor*, the genus *Aspergillus* or the genus *Penicillium*; or a lipase or an esterase derived from porcine pancreas.

9. A method for preparing an optically active naphthalene compound represented by formula [$A_1$]:

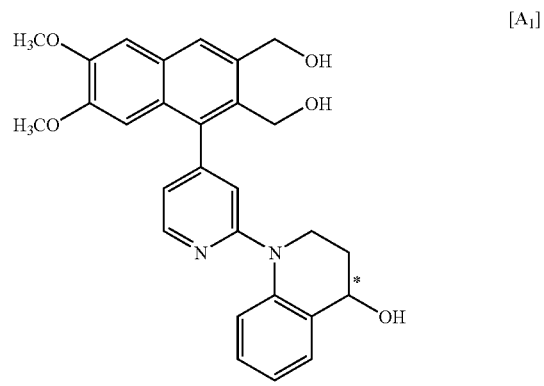

[$A_1$]

wherein * represents an asymmetric carbon atom which comprises the following steps of:
(1) treating a racemic 4-hydroxy-1,2,3,4-tetrahydroquinoline compound represented by formula [I]:

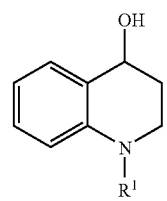

[I]

wherein $R^1$ represents a hydrogen atom or a protecting group for amino group
with an enzyme having an ability of selectively or preferentially acylating one enantiomer of the racemic compound [I] in the presence of an acyl donor to obtain a mixture of a 4-hydroxy-1,2,3,4-tetrahydroquinoline compound represented by formula [Ia]:

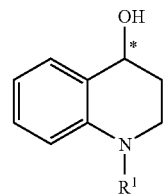

[Ia]

and a 4-acyloxy-1,2,3,4-tetrahydroquinoline compound represented by formula [II]:

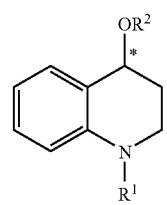

[II]

wherein R² represents an acyl group,
which is an acylated product of the corresponding enantiomer of the compound [Ia];
(2) separating the compound [Ia] from the mixture obtained in the step (1), or
separating the compound [II] from the mixture and then subjecting the compound [II] to solvolysis, to obtain an optically active 4-hydroxy-1,2,3,4-tetrahydroquinoline compound [I];
(3) introducing a protecting group to a hydroxyl group at 4-position of the optically active 4-hydroxy-1,2,3,4-tetrahydroquinoline compound [I] obtained in the step (2) to obtain a compound represented by formula [IV]:

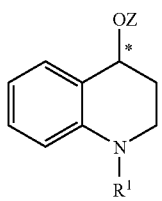

[IV]

wherein Z represent a protecting group for hydroxyl group,
(4) when the substituent (R¹) at 1-position of the compound [IV] is a protecting group for amino group, removing the protecting group to obtain an optically active tetrahydroquinoline compound represented by formula [V]:

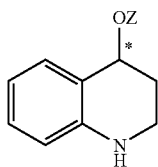

[V]

(5) reacting the compound [V] with a compound represented by formula [VI]:

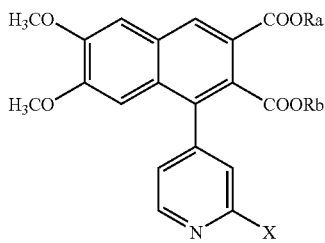

[VI]

wherein Ra and Rb represent a hydrogen atom or a protecting group for carboxyl group, and X represents a halogen atom
to obtain an optically active naphthalene compound represented by formula [VII]:

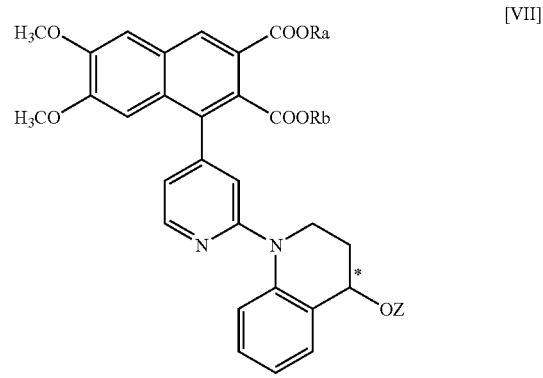

[VII]

(6) reducing the compound [VII] to obtain an optically active naphthalene compound represented by formula [VIII]:

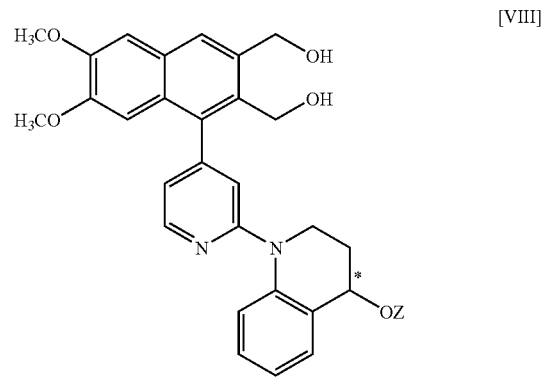

[VIII]

; and (7) removing the protecting group Z for hydroxyl group from the compound [VIII].

* * * * *